United States Patent [19]
Suzuki

[11] Patent Number: 4,649,276
[45] Date of Patent: Mar. 10, 1987

[54] HIGH-ENERGY RADIATION DETECTOR AND METHOD OF DETECTION

[75] Inventor: Arata Suzuki, Ramsey, N.J.

[73] Assignee: Capintec, Inc., Ramsey, N.J.

[21] Appl. No.: 711,096

[22] Filed: Mar. 13, 1985

[51] Int. Cl.[4] ............................ G01T 1/20; G21F 3/00
[52] U.S. Cl. ................................ 250/361 R; 250/362; 250/370; 250/390; 250/515.1
[58] Field of Search ............... 250/361 R, 362, 363 R, 250/363 S, 370 I, 390 J, 515.1

[56] References Cited

U.S. PATENT DOCUMENTS

| | | | |
|---|---|---|---|
| 2,688,095 | 8/1954 | Andrews | 250/366 |
| 2,739,242 | 3/1956 | Armistead | 250/366 |
| 3,039,000 | 6/1962 | Kieffer et al. | 250/515.1 |
| 3,087,060 | 4/1963 | Omohundro et al. | 250/361 R |
| 3,246,157 | 4/1966 | Reed et al. | 250/361 R |
| 3,538,328 | 11/1970 | Strausser | 250/361 R |
| 3,858,050 | 12/1974 | Carlson | 250/515.1 |
| 3,882,309 | 5/1975 | Paap | 250/264 |
| 3,883,741 | 5/1975 | Thumim | 250/328 |
| 3,890,505 | 6/1975 | Olson | 250/361 R |
| 3,950,647 | 4/1976 | Piltingsrud | 250/361 R |
| 4,060,730 | 11/1977 | Zioni et al. | 250/369 |
| 4,243,884 | 1/1981 | Avera, Jr. | 250/361 R |
| 4,383,175 | 5/1983 | Toepke | 250/368 |

FOREIGN PATENT DOCUMENTS 0009968 4/1980 European Pat. Off. .

OTHER PUBLICATIONS

F. Dydak, G. Laverrière, F. L. Navarria, P. Steffen, P. Schilly, E. G. H. Williams, H. Taureg and M. Vysocansk, "Performance of a Lead-Glass Detector for High-Energy γ-Rays" *Nuclear Instruments and Methods*, vol. 137, No. 3, (Sep. 15, 1976), pp. 427–434.

"An Ambulatory Ventricular Function Monitor: Validation and Preliminary Clinical Results," Wilson et al., Sep. 1, 1983 issue of *The American Journal of Cardiology*, pp. 601–606.

"Performance of Different Phoswich Configurations in a Balloon Flight Experiment", by F. Frontera et al., *Nuclear Instruments and Methods in Physics Research*, (Apr. 1985), vol. A235, No. 3, pp. 573–581.

*Primary Examiner*—Janice A. Howell
*Assistant Examiner*—Constantine Hannaher
*Attorney, Agent, or Firm*—Fleit, Jacobson, Cohn & Price

[57] ABSTRACT

A high-energy radiation detector includes a collimator, coupled to one end of a scintillator and the other end of the scintillator optically coupled to an optical window. The optical window is composed of a material having a predetermined amount of heavy metal therein. The optical window is further coupled to a photomultiplier which generates an electrical signal based upon the amount of light directed thereon. A radiation shield extends only around the scintillator and around limited portions of the optical window to minimize the weight of the radiation detector. A method for detecting high-energy radiation includes the steps of collimating the radiation, transforming the collimated radiation into light, optically channeling the light, converting the channeled light into an electrical signal, and shielding the non-collimated radiation which would have been transformed due to the directional orientation of that non-collimated radiation by excluding said non-collimated radiation during the optical channeling of the light and by further excluding the non-collimated radiation from the immediate vicinity of the transformation of the collimated radiation.

9 Claims, 6 Drawing Figures

FIG. I.
(PRIOR ART)

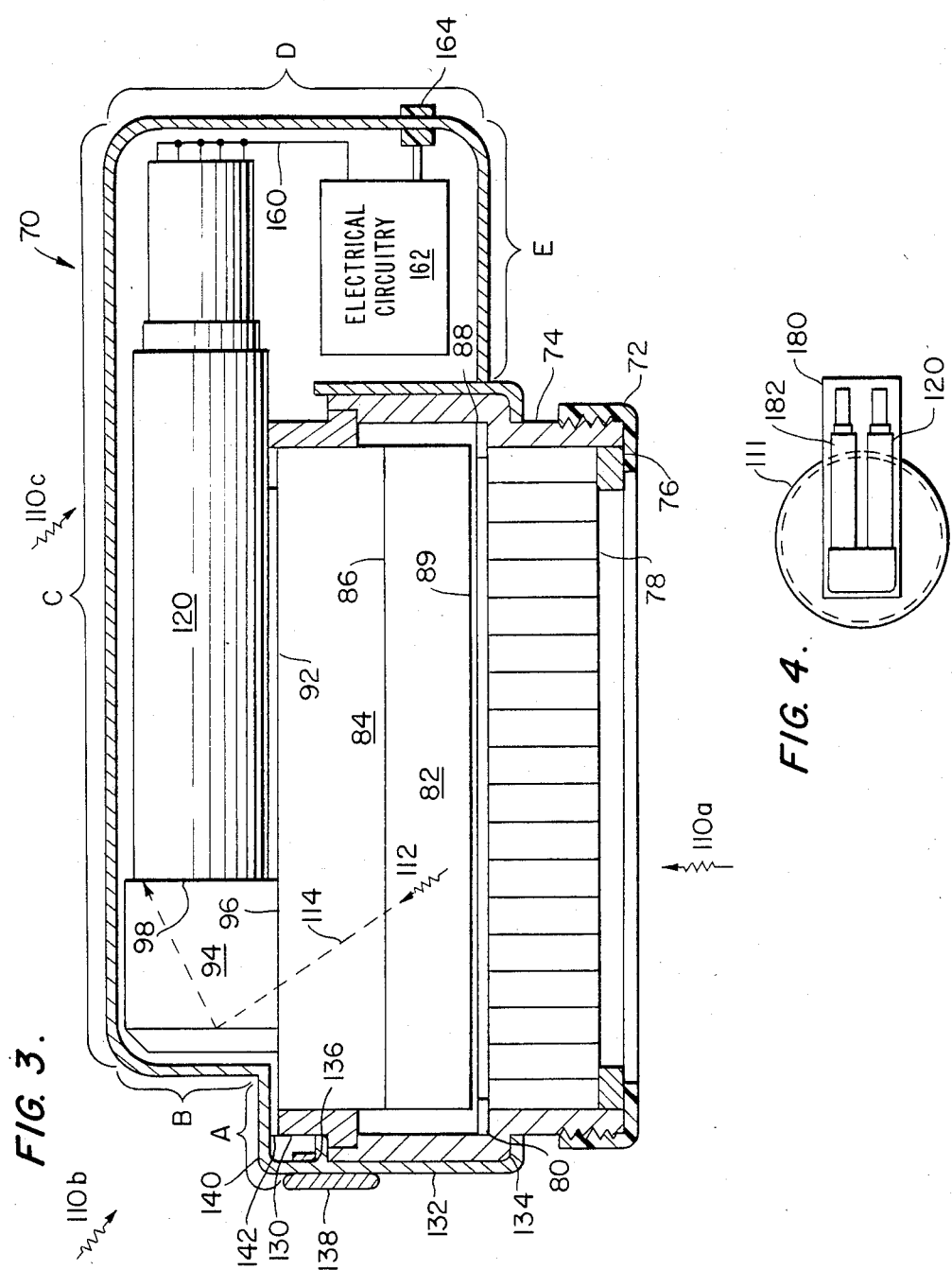

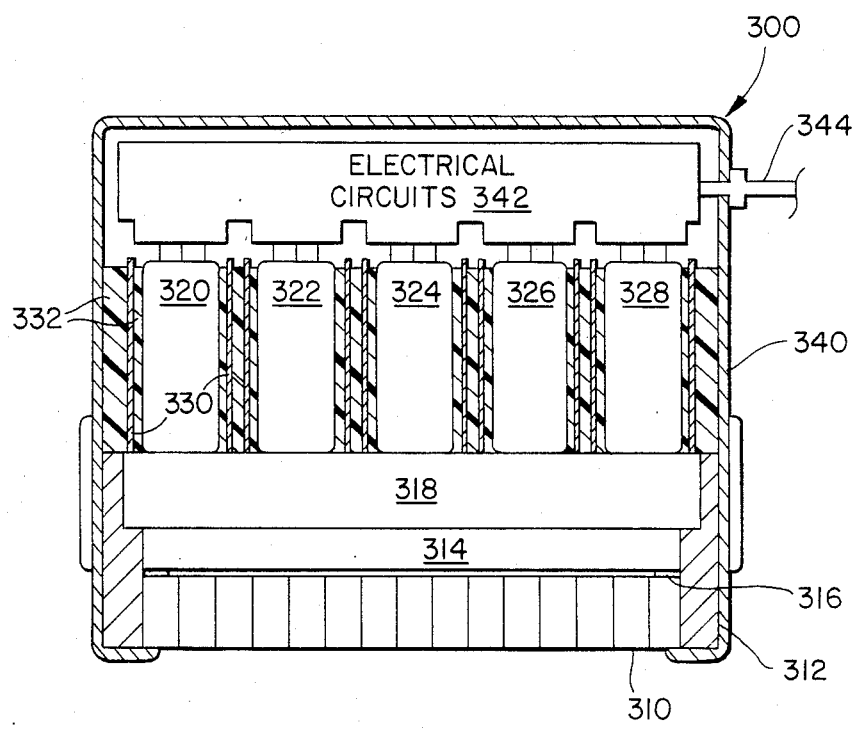

HIGH-ENERGY RADIATION DETECTOR AND METHOD OF DETECTION

BACKGROUND OF THE INVENTION

This invention relates generally to radiation detectors, and particularly to detectors utilized in the nuclear medicine field. Also, this invention relates to a method of detecting high energy radiation.

Radiation detectors capable of sensing high-energy radiation particles such as x-rays, gamma rays, photons, electrons, and neutrons (in general 20 keV and higher), are susceptible to background radiation. If the source radiation or radiation emitted by the object under test varies substantially or is minimal, the background radiation interferes with the sensing capabilities of the detector and ultimately dilutes and distorts the signal obtained from the detector. In that instance, the output signal poorly represents the radiation sought to be detected.

To minimize the effect of this background radiation or non-source emitted radiation, prior art devices utilize lead shielding surrounding the entire detector assembly to exclude the background and other non-source radiation from impinging upon critical parts of the detector.

Detectors utilized in the nuclear medicine field are very susceptible to spurious, background radiation because only a limited amount of a radioactive substance is injected into the person or other living being under test to obtain an anatomical image or to monitor the physiology of an organ. A typical radionuclide utilized for medical diagnosis is technetium-99 m which emits gamma rays at 140 keV. Other radionuclides are iodine 123 which emits gamma rays at 159 keV; Xe-133, 81 keV $\gamma$-ray; T$\gamma$-201, 70 keV x-ray and 279 keV $\gamma$-ray; etc. For example, a small amount of red blood cells (RBCs) are initially labeled with technetium-99 m, (Tc-99 m) and those labeled cells are thereafter injected into the blood stream of a patient (or RBC are labeled with Tc-99 m in vivo) to conduct diagnosis of heart function. A gamma ray camera or a detector assembly (cardiac monitor) is utilized in such a test.

Recently, there is a need for an ambulatory cardiac monitor which is placed onto a patient to monitor the patient's physiological activities during a prescribed period of time. The ambulatory cardiac monitor is placed generally over the heart of the patient and the high-energy detector, mounted within the monitor, senses the ebb and flow of blood through the heart by detection of the gamma rays emitted by the Tc-99 m labeled blood cells. The precise measurement of the gamma rays, emitted by the labeled blood cells, contains a wide range of cardiac information which is helpful in diagnosing, among other things, cardiac disorders. However, the precision of the cardiac monitor is highly dependent upon the ability of the monitor to detect only the gamma rays emitted by the technetium-99 m in the heart to the exclusion of background radiation and spurious radiation present in the other part of body and the ambient environment.

Prior art cardiac monitors, and other types of high-energy radiation detectors, commonly include one or more scintillators or means for detecting radiation which react to the radiation by emitting light of a predetermined wavelength. These scintillation detectors and associated electronic circuits are normally mounted within a lead shield such that radiation emitted from a predetermined source or emanating from a predetermined direction is collimated to impinge upon the scintillators. The light from the scintillators is channeled into some type of photo-detection device which converts the light into an electrical signal. One type of photo-detector commonly utilized is a photomultiplier tube.

The electrical signal output from the photomultiplier tube is applied to a cable which electronically links the monitor to complementary data processing equipment or display means. To insure that only radiation emanating from a certain source or from a certain direction affects the scintillator or scintillation crystals, a lead shield normally extends and surrounds the scintillator, the photomultiplier tube and further includes a lead back shield is utilized to exclude background radiation, traveling in a direction opposite the source emitted radiation, from impinging on scintillator. The use of this extensive lead shielding greatly increases the weight of a cardiac monitor.

In a similar fashion, the weight of other high-energy radiation detectors is greatly affected by the lead shielding normally surrounding substantially all of the detector assembly.

OBJECTS OF THE INVENTION

It is an object of this invention to reduce the weight of high-energy radiation detector assemblies by eliminating a substantial portion of the lead shielding.

It is another object of this present invention to achieve higher efficiency within the radiation detector by improving the match between the optical characteristics of the components in the detector.

It is a further object of the present invention to decrease the weight of the nuclear radiation detector utilized as a cardiac monitor, such that the device can be utilized in an ambulatory manner by a patient.

SUMMARY OF THE INVENTION

A high-energy radiation detector includes a means for detecting a predetermined type of high energy radiation, such as a crystal scintillator, and for transforming the detected radiation into light. The light from the scintillator is channeled through an optical window which is composed of a material having a predetermined amount of heavy metal therein, such as a window composed of leaded glass or flint glass. A photomultiplier tube generates an electrical signal due to the light channeled therein by the optical window. A collimator is mounted at one end of the scintillator to collimate the radiation sought to be detected. The collimator, in one embodiment, is lead. A shield of heavy metal, such as lead, extends over and covers specific portions of the scintillator crystal, those portions which are not open to the collimator or not optically coupled to the optical window and covers portions of the optical window. Since, the shielding covers only limited portions of the scintillator crystal and limited portions of the optical window, the weight of the radiation detector is minimized. A housing supports the collimator, shielding, scintillator, optical window, photomultiplier tube and associated circuitry as is recognized in the art.

A method of detecting high-energy radiation includes the steps of collimating the radiation, transforming the collimating radiation into light, optically channeling the light, converting the channeled light into an electrical signal, and shielding only the non-collimated radiation which would have been transformed due to the directional orientation of that non-collimated radiation by (1) excluding the non-collimated radiation during the optical channeling of the light and (2) excluding the non-collimated radiation from the immediate vicinity of the transformation of the collimating radiation. The transforming step is accomplished by scintillation of a crystal and the converting step is accomplished by photomultiplying the channeled light to obtain the electrical signal.

BRIEF DESCRIPTION OF THE DRAWINGS

The subject matter which is regarded as the invention is particularly pointed out and distinctly claimed in the concluding portion of the specification. The invention, however, together with further objects and advantages thereof, may best be understood by reference to the following description taken in connection with the accompanying drawing in which:

FIG. 3 illustrates a cross-sectional view of an ambulatory cardiac monitor constructed in accordance with the present invention;

FIG. 4 illustrates the top-view of the ambulatory cardiac monitor shown in FIG. 3;

FIG. 6 illustrates a schematic of a gamma ray camera in accordance with the present invention.

DETAILED DESCRIPTION OF EMBODIMENTS OF THE INVENTION

The present invention relates to a high-energy radiation detector, and particularly relates to detectors capable of sensing radiation emitted from a particular source or emanating from a particular direction and a method for detecting such radiation.

Figure 1:
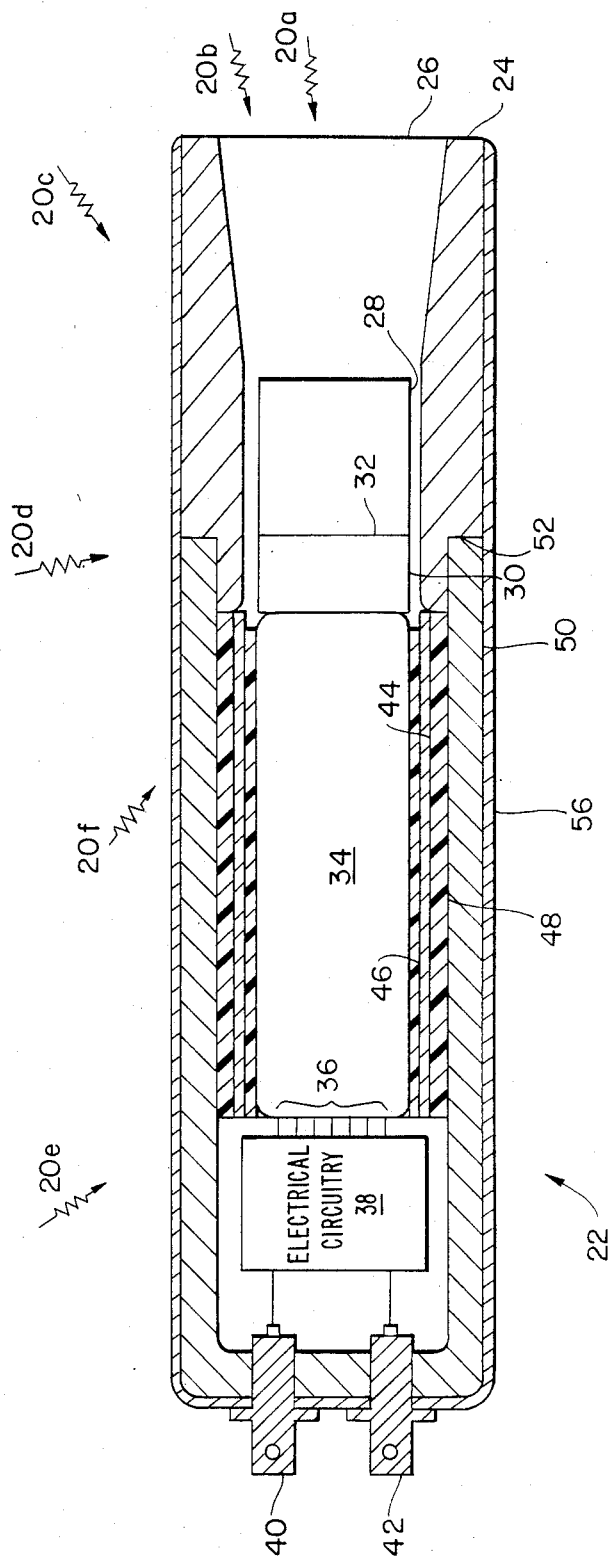
FIG. 1 illustrates a cross-sectional view of a prior art radiation detector.

FIG. 1 is a cross-sectional illustration of a prior art radiation detector 22. As utilized herein, the term "high-energy radiation" refers to x-rays, or gamma rays, and charged particles, such as protons and electrons, and non-charged particles such as neutrons. In a preferred embodiment, the high-energy radiation results from the transition of the meta-stable state to ground state of technetium-99 (Tc 99 m) which emits gamma rays of 140 keV. In another embodiment, the high-energy radiation is the 159 keV gamma rays from the decay of iodine 123. In general, the energy range of the high-energy radiation extends 20 keV to 660 keV for diagnostic medical applications. For illustration purposes only, high energy radiation particles 20a, b, c, d, e, and f are shown in FIG. 1.

The prior art radiation detector 22 is a generally cylindrical elongated body which includes collimator 24. Collimator 24 has an open end 26 adopted to admit high-energy radiation particles 20a, b and collimate the same on to scintillator 28 which is the means for detecting the predetermined type of high-energy radiation. Scintillator 28 transforms the collimated radiation into light. In a preferred embodiment, scintillator 28 is a thallium activated sodium iodide NaI(Tl). However, other types of scintillators, such as thallium activated cesium iodide CsI(Tl), or organic scintillators, such as plastic (polystyrene) scintillator or liguid scintillator (polyvinyltoluene) counter or spectrometer can be utilized in the detector. In operation, scintillator 28 is excited by or reacts with, in the preferred embodiment, the gamma rays and emits a photon as a result of the reaction. As is commonly recognized, different scintillators react to different types of high-energy radiation. Likewise, different types of scintillators emit different energies of photons or wavelengths of light during the scintillation event. Hence, election of the appropriate scintillator depends upon the specific type of radiation sought to be detected.

Collimator 24, in this prior art device, is composed of lead or lead alloy. As is recognized in the art, the beforementioned high-energy radiation can be shielded by lead or other types of non-radioactive heavy metals such as Bi, or W, and alloys thereof. The term "heavy metal", as used herein, refers to those types of heavy metals and other types of metals impervious and impenetrable by the high-energy radiation. As illustrated in FIG. 1, only gamma rays 20a, b are collimated by collimator 24 onto scintillator 28. Gamma ray 20c, due to its directional orientation, would be excluded and shielded from scintillator 28 by the collimator.

Some of the photons, light emitted during a scintillation event, in scintillator 28 are transmitted through optical window 30, which is sometimes referred to as a light pipe. Commonly, optical window 30 is composed of borosilicate glass. Optical window 30 is optically coupled to end 32 of scintillator 28. As is recognized in the art, optical window 30 is affixed to scintillator 28 by an epoxy or such as RTV®, a type of scilicon based composition manufactured by General Electric Company. Optical window 30 channels the light from scintillator 28 into photomultiplier 34. The interface between optical window 30 and photomultiplier 34 is conventionally sealed with optical grease.

Photomultiplier tube 34 converts the light or photons directed therein to an electrical signal and outputs the same via one or more pins 36 to electrical circuitry 38. Electrical circuitry 38 provides power to photomultiplier 34 and amplification for the output signal from photomultiplier 34. Power to electrial circuitry 38 and the signals from circuitry 38 are applied to terminals 40, 42, extending outboard of detector 22. The operation of photomultiplier 34 and electrical circuitry 38 is well known in the art.

To reduce interference by external electromagnetic fields, electromagnetic shield 44 surrounds a substantial portion of photomultiplier 34. Commonly, electromagnetic shield 44 is composed of mu metal. Electromagnetic shield 44 is sandwiched between support material 46, 48, which is commonly some type of sponge or other inert material such as rubber.

The prior art device in FIG. 1 includes radiation shield 50 which mates interlockingly at end 52 with collimator 24. As clearly illustrated in FIG. 1, radiation shield 50 extends over portions of optical window 30, over the entirety of the photomultiplier 34, extends over the entirety of electrical circuitry 38, and is sealingly, disposed about terminals 40, 42, to completely enclose and shield those items from non-source radiation. Radiation shield 50 is a heavy metal which is commonly lead. Radiation shield 50 excludes gamma rays 20d, e, and f from impinging on photomultiplier 34 and/or scintillator 28. As is easily recognized in FIG. 1, gamma ray 20e, due to its directional orientation, would not impinge scintillator 28 if radiation shield 50 were removed. However, as is recognized in the art, gamma ray 20e could be deflected or scattered by components within photomultiplier 34 and thereafter be directed axially along radiation detector 22 into scintillator 28. A housing 56 encloses collimator 24 and shield 50.

Figure 2:
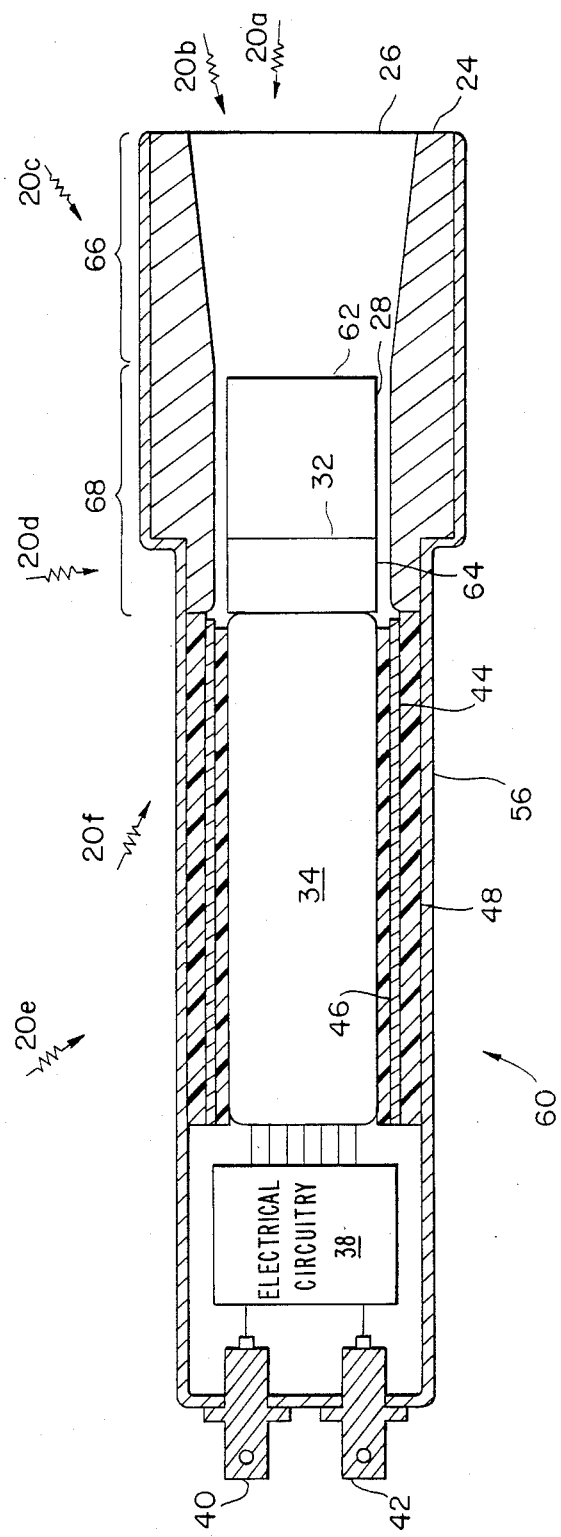
FIG. 2 illustrates a cross-sectional view of a radiation detector in accordance with the present invention.

FIG. 2 illustrates, in cross-section, radiation detector 60 constructed in accordance with the present invention. Similar numbers designating similar items have been carried forward throughout the figures. One of the differences between the prior art device illustrated in FIG. 1 and the embodiment of the present invention, illustrated in FIG. 2, is the absence of radiation shield 50. In FIG. 2, gamma rays 20a, b, are collimated by collimator 24 as they enter end 26 and pass through the illustrated portions of collimator 24. Thereafter, gamma rays 20a, b, impinge end 62 of scintillator 28. The material in scintillator 28 is excited by the gamma rays and photons (light) are generated within scintillator 28. A portion of the photons generated within scintillator 28 pass through end 32 into optical window 64. In the present invention, optical window 64 is composed of a material having a predetermined amount of heavy metal therein. In the preferred embodiment, optical window 64 is a heavy flint glass which is commonly recognized as leaded glass. An example of such glass is dense flint glass, manufactured by Hoya Optics, Inc., of Fremont, Calif., which has the following characteristics:

glass group: dense flint
glass type: FD-8
index of refraction: n=1.718
specific gravity: 4.21
80% transmission (1 cm sample): 390 nm
5% transmission: 340 nm
lead content by wt: 50%
lead content by thickness: 23%

Although this type of dense flint glass is utilized in the present embodiment, other suitable optical material can be used such as a less costly flint glass having 40% lead or lead containing plastic utilized with the scintillator described earlier. Other types of leaded glass are identified as type EDF or DF from Bausch and Lomb Company. Optical window 64 channels the light from end 32 of scintillator 28 into photomultiplier 34. Additionally, optical window 64 is impervious to gamma rays 20d and 20f. In this fashion, optical window 64 shields the non-collimated radiation during the optical channeling of the light therethrough.

The present invention eliminates radiation shield 50 because scintillator 28 is shielded on all sides, other than end 62, from spurious, background or other non-collimated radiation. Collimator 22 includes collimating portion 66 and shielding portion 68. Collimating portion 66 collimates the radiation sought to be detected by detector 60, whereas shielding portion 68 shields scintillator 28 and portions of optical window 64 from non-collimated radiation, such as gamma ray 20d. As clearly illustrated in FIG. 2, shielding portion 68 is limited to, extends over and covers scintillator 28 other than end 62 and end 32. Further, shielding portion 68 extends over portions of optical window 64. The weight of radiation detector 60 is substantially reduced and minimized due to the limited extent of portion 68 of collimator 24. As utilized herein, the term "limited extent" or the term "being limited to" refers to shielding portion 68 extending over and covering those portions of scintillator 62 other than ends 32 and 62, and further extending over and covering at least the interface between optical window 64 and scintillator 28. Those terms do not refer to shielding portion 68 extending over photomultiplier tube 34 and beyond to circuitry 38. The absence of the extensive lead radiation shield (shown as shield 50 in FIG. 1) greatly reduces the weight of detector 60. It is estimated that a typical weight reduction of 50% can be achieved with the present invention.

The method of detecting high energy radiation, according to the present invention, includes the steps of collimating the radiation passing through portion 66 of collimator 22 (particles 20a, b), transforming the collimated radiation into light by scintillator 28, optically channeling the light, via optical window 64, converting the channeled light into an electrical signal due to the operation of photomultiplier 34, and shielding only the non-collimated radiation which would have been transformed due to the directional orientation of that non-collimated radiation. In other words, gamma ray 20c is shielded by collimating portion 66 of collimator 24 and is excluded thereby from interacting with scintillator 28 due to the heavy metal content of collimator 24. Non-collimated gamma ray 20d is shielded by shielding portion 68 of collimator 24. Non-collimated gamma ray 20f is shielded by optical window 64 due to the directional orientation of that particle and the lead content of the window. Hence, gamma rays 20c, d and f are excluded from the immediately vicinity of the transformation of the collimated radiation, i.e., the immediate vicinity of the scintillator. As used herein, the term "immediately vicinity" refers to the space occupied by scintillator 28.

The shielding utilized in the present invention is limited to selected portions of scintillator 28 and selected portions of optical window 64. Hence, non-collimated gamma ray 20e is not shielded, excluded, blocked or otherwise effected since that ray's directional orientation is such that the ray would not impinge on scintillator 28 and hence would not be detected along with the collimated radiation. Even if gamma ray 20e is scattered or deflected by an element in photomultiplier 34, optical window 64 provides an axial end shield for such high-energy radiation directed towards scintillator 28.

The amount of shielding utilized in a particular radiation detector depends upon the type of radiation sought to be detected. In the nuclear medicine example described herein, wherein gamma rays of 140 keV are detected as they are emitted by the Tc 99, the lead shield of the prior art device is approximately ⅛th of an inch thick (0.3 cm). In the present invention, that lead shield is eliminated and the optical window 30, in the prior art device, is replaced by optical window 64 of dense flint glass, approximately ⅜ inch thick (0.9 cm). A 50% reduction in weight is noted by eliminating the lead radiation shield 50 from the prior art device.

It is commonly recognized that the optical transmittance characteristic of the optical window, i.e., the refractive index n, should be matched with the refractive index of the scintillator. The present invention improves light detection efficiency beause the refraction index n of the scintillator is better matched to the refractive index n of the dense flint glass. The index of refraction of NaI(Tl) is 1.77; the index of refraction of the Hoya dense flint FD-8 glass is 1.718; whereas the index of refraction of borosilicate glass is 1.52. In a preferred embodiment, photomultiplier 34 is a bialkali photocathode, Model No. R1635 (or R1639, etc.), manufactured by Hamamatsu of Middlesex, New Jersey. The spectral sensitivity of the Hamamatsu photocathode is maximum at 370 nm and the wavelength of scintillation from NaI(Tl) peaks at 405 nm and has a cut off point at 390 nm.

It is well known that light will be totally reflected at a surface of the interfacing plane between two materials if the angle between the light ray and the plane normal to the surface is greater than the critical angle. $\theta_c = \sin^{-1}(n_2/n_1)$ wherein, $n_1$ is the index of refraction of one media (e.g., scintillator 28) and $n_2$ is the index of refraction of the adjoining optically transparent media (e.g., optical window 64). The present invention improves the optical characteristics of the radiation detector because the ratio $n_2/n_1$ is closer to unity (1.718/1.77) as compared with the prior art device (1.52/1.77). The reduction of light reflected at the interface improves the efficiency of the detector because less light is reflected at the interface and hence more light enters the optical transmission path to the photomultiplier tube.

Other types of light detectors may be substituted for photomultiplier 34 including, but not limited to, photocells, photodiodes, photodiode arrays, photo-sensitive avalanche diodes, phototransistors, diode image matrices, microchannel plates, image intensifiers. RCA manufactures a 10-stage photomultiplier tube and Hamamatsu manufactures microchannel plates which can be utilized in the present invention. In any event, the light detecting means, i.e. photomultiplier 34, must be compatible with the wavelength of light emitted by scintillator 28. Elecromagnatic shield 44 can be composed of mu metal having a typical thickness between 0.5 mm-1 mm and which surrounds or wraps photomultiplier 34. In one embodiment, housing 56 is composed of either aluminum or plastic. The mounting of items within radiation detector 60 is well known in the art and the choice of mounting does not substantially effect the present invention. Further, support material 46, 48 may be eliminated such that an air gap or void exists between one or more of the components such as photodetector 34, electromagnetic shield 44, and housing 56.

FIG. 3 is a cross-sectional illustration of an ambulatory cardiac monitor 70 constructed in accordance with the present invention. Cardiac monitor 70 is utilized in a specific embodiment to detect Tc 99 during radionuclide testing. A cover 72, preferably composed of nylon, is threadably mounted on shield 74 which is preferably lead with 5% antimony therein and approximately 0.1 inches thick. Iris 76 spaces collimator 78 from cover 72. Collimator 78, iris 76, cover 72 and shield 74 are generally circular as illustrated in FIG. 4, at circular portion 111. In a preferred embodiment, collimator 78 is composed of lead and is a septa material which has a cross-sectional flat hole size of 0.070 inches (0.178 cm), a septa thickness of 0.010 inches (0.025 cm), an overall thickness of 0.4 inches(1 cm), and a diameter of 2.25 inches (5.72 cm) to collimate gamma rays having an energy of 140 keV. The dimensions presented herein are rough estimates of a working embodiment of the invention. Iris 76 is composed, in the preferred embodiment, of lead.

Circular gasket 80 space collimator 78 from scintillator 82 which is an NaI(Tl) scintillator in this embodiment and it is supported in an aluminum enclosure 88 with reflective surface 89. Optical window 84 has a polished end 86 proximate one end of scintillator 82 and a polished end 92. Light guide 94 has polished ends 96 and 98, and polished end 96 is adjacent to a portion of polished end 92 of optical window 84. In this embodiment, optical window and light pipe corresponding to optical window of scintillator assembly 28 and light pipe 30 of prior art shown in FIG. 1 are combined in one item, 84. Optical window 84 and light guide 94 are composed of the aforementioned dense flint glass manufactured by Hoya Optics in this embodiment.

In operation, gamma ray 110a is emitted from the detectable source and gamma rays 110b, c are present in the ambient environment about cardiac monitor 70. Gamma ray 110a is collimated by collimator 78 and reacts with scintillator 82. For illustration purposes only, a photon 112 is shown as generated in scintillator 82 which follows a path noted by dashed line 114 through the optical transmission path including optical window 84 and light guide 94. The ultimate destination of photon 112 is photomultiplier 120 which generates an electrical signal based upon that photon which was directed therein by the optical transmission path. In a preferred embodiment, photomultiplier 120 has ten-stages wherein an increasing larger number of electrons are generated at each stage based initially upon a light passing through the interface of end 98 and the photomultiplier tube.

Cardiac monitor 70 also includes auxiliary leaded shielding ring 130 circumferentially surrounding portions of optical window 84. In a preferred embodiment, auxiliary lead shielding ring 130 includes 5% antimony. Retaining housing 132 mates with end 136 of rearward housing 140. Retaining belt 138 fixes housing 140 to retaining member 132. Photomultiplier 120 is conventionally mounted within housing 140.

Power is supplied to photomultiplier 120 and signals are obtained therefrom by the schematically illustrated electrical connection 160 coupling photomultiplier 120 to electrical circuitry 162. A conventional output plug means 164 provides coupling between power and data processing apparatus, (not shown) and electrical circuitry 162.

The sectors designated A, B, C, D, and E illustrated by dashed lines about cardiac monitor 70, would, in a prior art device, be shielded by a lead shield. Lead shielding about sectors A, B, C, D, and E is required in prior art devices because gamma ray 110b would be detected by scintillator 82 but for the lead shielding at sectors A, B, C, D, and E. However, in the present invention, optical window 84 is composed of a material having a predetermined amount of heavy metal therein, e.g., lead, therefore, gamma ray 110b is excluded from the immediate vicinity of scintillator 82. In contrast to prior art devices, gamma ray 110c is not shielded in the present invention since the directional orientation of that gamma ray is such that the ray would not enter the immediate vicinity of and be detected by scintillator 82. In other words, the present invention shields only non-collimated radiation which would be transformed due to the directional orientation of that non-collimated radiation. The exclusion of non-collimated radiation occurs because of the lead content of optical window 84, auxiliary lead shielding ring 130, and light guide 94, and the lead shield 74 which collimates the gamma rays and also shields selected portions of scintillator 82. Housing 140 is composed of aluminum in this embodiment.

The approximate dimensions of one working embodiment of cardiac monitor 70 are as follows: the diameter of circular portion 110 in FIG. 4 is approximately 2.5 inches (6.4 cm); scintillator 82 is approximately 0.25 inches (0.64 cm) thick; the thickness of monitor 70 is approximately 1.8 inches (4.6 cm); and the rectangular portion 180 in FIG. 4, housing photomultiplier, 120 and photomultiplier 182, has a length of 3.3 inches (8.4 cm) and a width of 1.3 inches (3.3 cm). As is commonly recognized in the art, photomultipliers 120, 182 may be electromagnetically shielded by mu metal, however, such electromagnetic shielding is not specifically illustrated in FIG. 3. Further, the space between housing 140 and photomultiplier 120 may either be filled with sponge, rubber or other inert material; or be an air gap.

Due to the relatively small dimensions of cardiac monitor 70, the inclusion of a lead shield about sectors of A, B, C, D, and E significantly increases the weight of a device. Hence, the present invention is lighter in weight than the prior art monitor, to wit, approximately 50% lighter. Further, the light detection efficiency of cardiac monitor 70 is improved due to the closer match between the index of refraction n of the dense flint glass utilized for optical window 84, and light guide 94, and the n value of scintillator 82.

Figure 5:
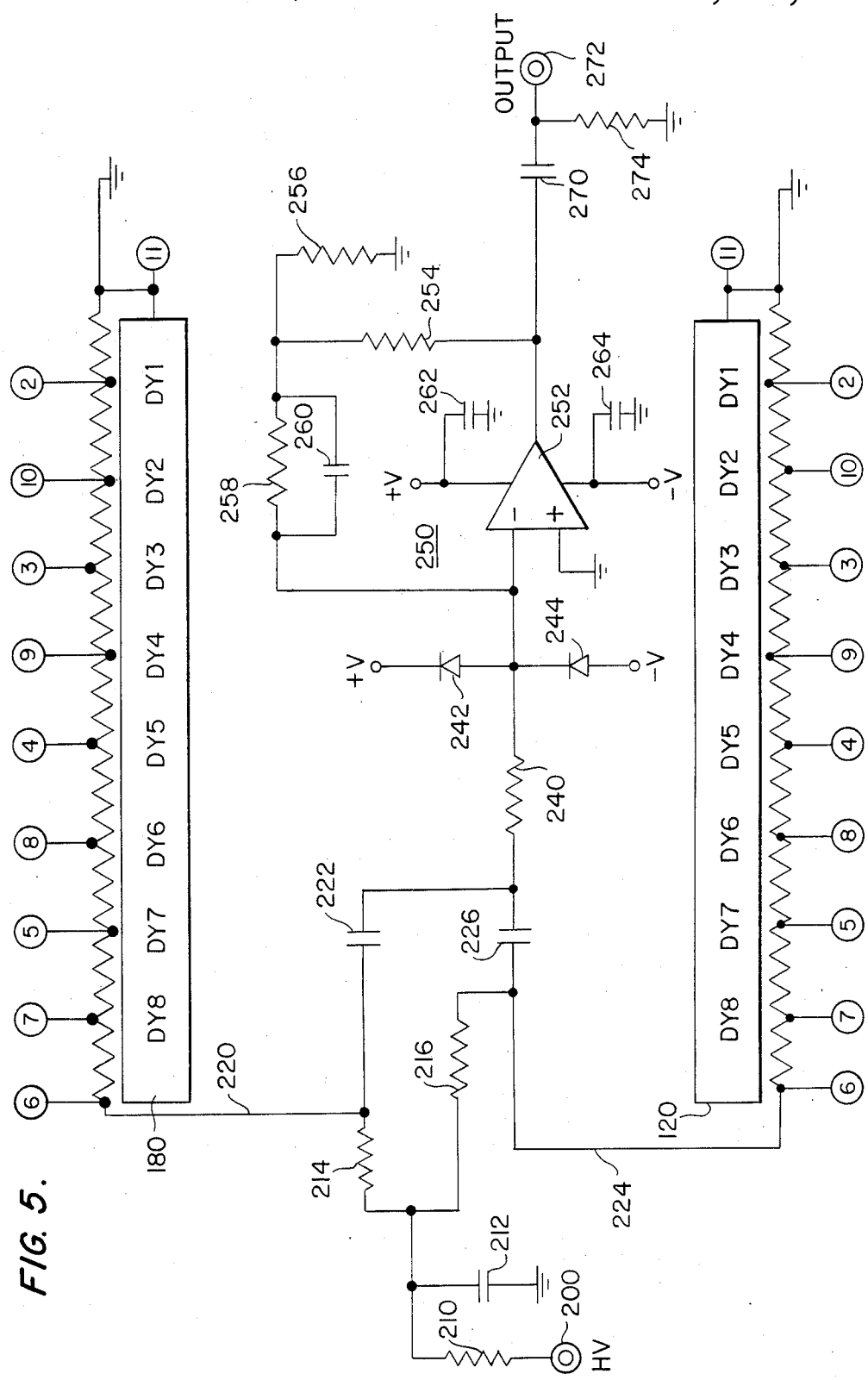
FIG. 5 illustrates a schematic of the electrical circuitry for the ambulatory cardiac monitor illustrated in FIG. 3.

FIG. 5 shows an electrical schematic of electrical circuitry 162. High voltage (HV) is applied at point 200 and passes through resistor 210 to one side of decoupling filter capacitor 212. Load resistors 214 and 216, preferably one mega ohm resistors, are coupled to photomultipliers 180, 120, respectively. Line 220 transmits power to photomultiplier 180 as well as carries the output signal to coupling capacitor 222. Line 224 carries power and the output signal to and from photomultiplier 220 and is coupled to one side of coupling capacitor 226. Photomultipliers 120 and 180 are illustrated as having dynodes DY 1–8. Pins 2, 3, 4, 5, 6, 7, 8, 9, 10, and 11 are illustrated on photomultipliers 120, 180. The resistors interposed between those pins represent voltage dividers as is recognized in the art.

Coupling capacitors 222 and 226 isolate the high voltage power from the balance of the signal processing circuitry and pass only the AC signal to lines 220 and 224, respectively. The signals passed by capacitors 222, 226 are the pulses generated by the photomultipliers resulting from the detection of photons. A limiter circuit, including resistor 240, 241, diode 242, and diode 244 couples capacitors 222, 226 to amplification circuit 250. Positive and negative voltages are applied to the opposite sides of diodes 242, 244. Amplification circuit 250 includes operational amplifier 252, gain setting resistors 254, 256, and feedback components including resistor 258 and capacitor 260, both of which establish the time constant for operational amplifier 252. Voltages are applied to operational amplifier 252 at capacitors 262, 264 which decouple the positive and negative voltage supplied thereto. Coupling capacitor 270 links the output of amplification circuit 250 to output pin 272 and resistor 274 keeps a ground potential on the output. In one embodiment, the output on pin 272 is a 50 millivolt pulse having a 2 microsecond decay time constant. Output terminal 272 is linked to data processing equipment, not shown, to further process the signal as is recognized in the art.

FIG. 6 illustrates a cross-sectional view of a gamma camera, constructed in accordance with the present invention. Gamma camera 300 includes lead collimator 310 and lead frontal side shield 312. Scintillator 314 is spaced from collimator 310 by circular gasket 316. The end of the scintillator opposite collimator 310 is adjacent an optical window 318 which is composed of leaded glass as described in detail hereinabove. Photomultipliers 320, 322, 324, 326 and 328 are positioned to receive light generated by scintillator 314 and transmitted through optical window 318. Each photomultiplier is surrounded by electromagnetic shielding. One electromagnetic shield 330 is numerically identified as surrouding photomultiplier 320. The plurality of photomultipliers are supported within housing 340 by sponge or rubber, one of which is sponge 332 intermediate housing 340, electromagnetic shield 330 and photomultiplier 320.

Electrical circuits 342 provide power to the photomultipliers and receive the output signals from those photomultipliers and process the same in a manner well known to those of ordinary skill in the art. The output from electrical circuits 142 is applied to external cable 344. In a similar fashion to that noted above with respect to the radiation detector and the cardiac monitor, gamma camera 330 need not include additional lead shielding surrounding the photomultipliers and the electrical circuits as is common in prior art devices. Optical window 318, composed of leaded glass, effectively shields scintillator 314 as does frontal side shield 312 from non-collimated radiation.

The present invention, as claimed in the appended claims, is not meant to be limited by the specific embodiments disclosed herein. The positioning and the specific construction of the optical transmission path, from the optical window to the photomultipliers is purely exemplary in nature since light pipes can be interposed therebetween to obtain other optical transmission paths for chanelling the light to the photmultipliers. A radiation detector constructed in accordance with the present invention utilizes a scintillator having on one side thereof an optical window and/or light pipe composed of a material having a predetermined amount of heavy metal to shield the high-energy radiation from the scintillator. Further, the present invention contemplates an additional shielding means surrounding portions of the scintillator which are not open to the collimator to exclude other non-collimated radiation. The weight, and hence the size, of a device constructed in accordance with the principles of the present invention is significantly reduced because further radiation shields extending beyond the scintillator are unnecessary, or required additional shield will be reduced. The claims appended hereto are meant to encompass all modifications readily apparent to those of ordinary skill in the art.

I claim:

1. A high-energy radiation detector comprising:
   means for detecting a predetermined type of high-energy radiation and transforming the detected radiation into light, said means for detecting having a first and second end;
   means for generating an electric signal based upon the amount of light directed thereon and for outputting said signal;
   an optical window means optically coupled to said first end of the detecting means for channeling the light therefrom into the generating means, said optical window being composed of material having a predetermined amount of heavy metal therein;
   a collimator made of heavy metal disposed at said second end of said detecting means, said collimator having an open end to admit said high energy radiation onto said second end of said detecting means;
   means for shielding composed of heavy metal and being exclusively limited to and covering said detecting means other than said first and second ends of said detecting means and limited to and covering portions of said optical window, and the weight of the radiation detector being minimized due to the limited extent of said shielding means; and means for supporting said detecting means, said generating means, said optical window, said collimator and said shielding means;

wherein said means for detecting is shielded from high-energy radiation on all sides by said optical window and said means for shielding except for said second end adjacent said collimator and the means for supporting does not shield high-energy radiation from components internal thereto.

2. A radiation detector as in claim 1 wherein said shielding means and the heavy metal composition of said optical window are impervious to said predetermined type of high-energy radiation.

3. A radiation detector as in claim 1 wherein the heavy metal is a non-radioactive metal from the group of Pb, Bi, and W, and alloys thereof.

4. A radiation detector as in claim 1 wherein said detecting means is a scintillation radiation detector, said generating means is a photomultiplier and said optical window is a light pipe composed of leaded glass.

5. A radiation detector as in claim 4 wherein said shielding means is made of Pb and wherein said shielding means only extends over said scintillation detector and the interface between said scintillation detector and said optical window.

6. Method of detecting high energy radiation comprising the steps of:
 collimating the radiation;
 transforming the collimated radiation into light;
 optically channeling said light;
 converting the channeled light into an electrical signal; and
 shielding only the non-collimated radiation which would have been transformed due to the directional orientation of that non-collimated radiation by excluding said non-collimated radiation during the optical channeling of said light and by excluding said non-collimated radiation from the immediate vicinity of the transformation of said collimated radiation.

7. A method as in claim 6 including the step of electromagnetically shielding electromagnetic radiation and excluding the same during said converting step.

8. A method as in claim 6 wherein said transforming step is accomplished by scintillation and said converting step is accomplished by photomultiplying said channeled light to obtain said electrical signal.

9. A scintillation detector assembly comprising a scintillator for detecting high-energy radiation and transforming same into light, a lead glass optical window at one end thereof, said scintillator having an exposed end for admitting radiation thereto, and a heavy metal shield surrounding only the balance of said scintillator, and means for converting said light into an electrical signal coupled to said optical window.

* * * * *